US006653101B1

(12) United States Patent
Cockett et al.

(10) Patent No.: US 6,653,101 B1
(45) Date of Patent: *Nov. 25, 2003

(54) RECOMBINANT DNA METHOD AND HOST CELLS

(75) Inventors: Mark Ian Cockett, Maidenhead (GB); Christopher Robert Bebbington, Windsor (GB); Geoffrey Thomas Yarranton, Winnersh (GB)

(73) Assignee: Alusuisse Holdings A.G., Neuhausen am Rheinfall (CH)

(*) Notice: Subject to any disclaimer, the term of this patent is extended or adjusted under 35 U.S.C. 154(b) by 18 days.

This patent is subject to a terminal disclaimer.

(21) Appl. No.: 09/704,800

(22) Filed: Nov. 3, 2000

Related U.S. Application Data (63) Continuation of application No. 09/110,153, filed on Jul. 6, 1998, now abandoned, which is a continuation of application No. 08/442,646, filed on May 16, 1995, now Pat. No. 5,866,359, which is a continuation of application No. 08/253,325, filed on Jun. 3, 1994, now abandoned, which is a continuation of application No. 08/088,112, filed on Jul. 9, 1993, now abandoned, which is a continuation of application No. 07/929,493, filed on Aug. 18, 1992, now abandoned, which is a continuation of application No. 07/573,295, filed as application No. PCT/GB90/00032 on Jan. 20, 1990, now abandoned.

(30) Foreign Application Priority Data

Oct. 1, 1989 (GB) .......................... 89004832

(51) Int. Cl.$^7$ .................... C12P 21/06; C12N 15/00; C12N 15/63; C12N 5/00; C12N 5/08
(52) U.S. Cl. ................ 435/69.1; 435/372.3; 435/320.1; 435/455; 435/377; 435/369; 435/358
(58) Field of Search ............................ 435/320.1, 325, 435/69.1, 455, 369, 358, 372, 172.3, 377, 240.1

(56) References Cited

U.S. PATENT DOCUMENTS

| | | | |
|---|---|---|---|
| 4,740,461 A | 4/1988 | Kaufman | |
| 5,024,939 A | 6/1991 | Gorman | |
| 5,866,359 A | 2/1999 | Cockett et al. | |

FOREIGN PATENT DOCUMENTS

| | | |
|---|---|---|
| EP | 0 245 949 | 11/1987 |
| EP | 0 282 330 | 9/1988 |
| EP | 0 309 237 | 3/1989 |
| WO | 8 801 291 | 2/1988 |

OTHER PUBLICATIONS

Mohan N. Kuppuswamy et al. Relationship between the Transforming and Transcriptional regulatory Functions of Adenovirus 2 E1a Oncogene, 159, 31–38 (1987).*

Brad Zerler et al. Adenovirus E1A Coding Sequences That Enable ras and pmt Oncogenes To Transform Cultured Primary Cells, Molecular And Cellular Biology, Mar. 1986, p. 887–899, vol. 6, No. 3.*
Kushner et al., 1990 Molec. Endocrinology 4(10):1465–1473.
ATCC Catalogue Bacti, Phage, rDNA vectors, 16$^{th}$ Ed. 1985, pp. 248–249.
Moran et al., 1986 Molec. Cell Biol. 6(10):3470–3480.
Stinski et al., 1985, J. of Virology 55(2):431–441.
Lillie et al., 1986 Cell 46 : 1043–1051.
Gaynor et al., 1984 Proc. Natl. Acad. Sci. USA 81 : 1193–1197.
Schneider et al., 1987 EMBO J. 6(7):2053–2060.
Nevins, Trends in Biochem. Sci. 16:435–439, 1991.
Mitchell et al., Science 245:371–378,1989.
Hawley, Trends in Biochem. Sci. 16:317–318,1991.
Heintz, Trends in Biochem. Sci. 16:393, 1991.
Katagiri et al., Trends in Genetics 8:22–27, 1992.
Guarente et al., Trends in Genetics 8:27–32, 1992.
Grinnell et al., "Trans–Activated Experssion of Fully Gamma–Carboxylated Recombinant Human Protein C, An Antithrombotic Factor", Bio/Technology 5:1189–1192 (1987).
Velcich et al., "Adenovirus E1a Proteins Repress Transcription from the SV40 Early Promoter", Cell 40:705–716 (1985).
Alwine, James C., "Transient Gene Expression Control: Effects of Transfected DNA Stability and trans–Activation by Viral Early Proteins", Molecular and Cellular Biology 5(5):1034–1042 (1985).
Gélinas et al, "The v–rel oncogene encodes a cell–specific tanscriptional activator of certain promoters", Onocogene 3:349–355 (1988).
Thomsen et al, "Promoter–regulatory region of the major immediate early gene of human cytomegalovirus", Proc. Natl. Acad. Sci. USA 81:659–663 (1984).
White et al., Journal of Virology 65(6):2968–2978 (1991).
Kuppuswamy et al, Virology, 159, 31–38 (1987).
Montell et al, Nature, 295, p 380–383, Feb. 4, 1982.
Schneider et al, The EMBO Journal, 6(7) pp 2053–5060, 1987.
Moran et al, Mol Cell Biology, Oct. 1986, pp 3470–3480, vol 6, No. 10.

* cited by examiner

*Primary Examiner*—James Ketter
*Assistant Examiner*—M Marvich
(74) *Attorney, Agent, or Firm*—Nixon & Vanderhye, P.C.

(57) ABSTRACT

The present invention provides a process and host cell for use in increasing the amount of a desired protein by a cell line. The process and the cell line use a first transcription unit containing a gene for a transactivator protein to control the transactivation of a second transcription unit such that the amount of the desired protein expression can be increased without adversely affecting the cell growth. Preferred transactivator proteins are derived from EIA.

13 Claims, 3 Drawing Sheets

RECOMBINANT DNA METHOD AND HOST CELLS

This is a continuation of application Ser. No. 09/110,153, filed Jul. 6, 1998, now abandoned, which is a continuation of 08/442,646, filed May 16, 1995, now U.S. Pat. No. 5,866,359; which is a continuation of 08/253,325, filed Jun. 3, 1994 abandoned; which is a continuation of 08/088,112, filed Jul. 9, 1993 abandoned; which is a continuation of 07/929,493, filed Aug. 18, 1992 abandoned; which is a continuation of 07/573,295, filed Sep. 25, 1990; which was originally filed as PCT/GB90/00032, filed Jan. 20, 1990 abandoned, the entire contents of which are hereby incorporated by reference in this application.

The present invention relates to a method for producing proteins by recombinant DNA technology and to permanently transfected host cells for use in the method.

In recent years, recombinant DNA technology has advanced to the stage where, in general, it is readily possible to prepare a gene, that is a DNA sequence which encodes a desired protein. The gene may encode only a desired product or may encode a pro- or prepro-protein which, after translation, is cleaved to produce the desired final product. The gene may be prepared, for instance, (1) by isolating messenger RNA (mRNA) and using this as a template for the production of complementary DNA (cDNA) by reverse transcription, (2) by isolating the natural gene from genomic DNA using appropriate probes and restriction enzymes, (3) by synthesizing the gene from its component nucleotides or (4) by using a combination of these techniques.

It is also well known that a prepared gene can be placed in a vector, such as a plasmid or phage vector, under the control of appropriate 5' and 3' flanking sequences which allow the gene to be transcribed into mRNA and then translated into protein. Many important 5' and 3' flanking sequences, such as translation start and stop codons, TATA boxes, promoters, enhancers and polyadenylation sites, have been identified. The part of a vector including the gene and the 5' and 3' sequences is herein referred to as a transcription unit.

In general, the skilled person will be able readily to construct an expression vector and use it to transfect or transform a host cell such that the host cell is able to produce the desired final protein product. A variety of host cells can be used. Early work was carried out using prokaryotic microorganisms such as E. Coli. These hosts had the disadvantages that they do not have the necessary mechanisms to cleave efficiently pro- or prepro- sequences from proteins, they are unable to glycosylate proteins, they cannot cope with genes containing introns, and they generally do not secrete the proteins when formed.

There has therefore been a tendency towards the use of eukaryotic host cells. These generally avoid most of the disadvantages of prokaryotic host cells. However, eukaryotic host cells generally have more stringent requirements for culturing and also have slower growth rates. It is therefore not readily possible to produce large quantities of a product merely by culturing a eukaryotic host cell transformed with an expression vector.

There has therefore been considerable effort expended on increasing the amount of product which can be produced by a single eukaryotic host cell. Two of the main factors which control the amounts of product which a host cell can produce are gene copy number and the efficiency of transcription of each gene copy. There have been a number of proposals for increasing host cell productivity either by increasing gene copy number or by increasing transcription efficiency for each gene copy.

The most common method used to increase gene copy number is selection for gene amplification. In gene amplification, for instance as described in EP-A-0 045 809 or U.S. Pat. No. 4,634,665, a host cell is transformed with linked or unlinked genes. The first gene encodes a desired protein and the second gene encodes a selectable marker, such as DHFR. Cell lines containing both genes are then cultured in ever increasing concentrations of a toxic agent, the effect of which is nullified by the product of the selectable marker gene. It has been found that those cell lines which survive in the higher concentrations of the toxic agent have an increased copy number of both the selectable marker gene and the desired product gene. Thus, the host cell having the amplified number of gene copies can produce a larger amount of the desired protein than the original cell lines.

A disadvantage of gene amplification is that it is a laborious task to produce a highly productive cell line. Moreover, once the cell line has been produced, it is frequently necessary to retain it in a culture medium containing a high level of the selective agent. If this is not done, the selective pressure is released and the excess copies of the genes for the selectable marker and the desired protein may be eliminated. Using a culture medium containing a toxic agent causes problems in the purification of the desired product.

Another approach to increasing productivity is to increase the efficiency of transcription for each gene copy. This can be achieved by selection of a promoter which can be switched on by a stimulus, such as a toxic agent or heat. Alternatively, the gene for the desired product may merely be put under the control of a strong promoter. Although these approaches have to a certain extent been successful, they have not totally succeeded in raising productivity to commercially desirable levels.

There is therefore a need for a method for increasing the productivity of eukaryotic host cells containing genes encoding desired proteins.

It has been known for some long time that there are viral genes which, when translated, produce activator proteins which cause the activation of other genes in the viral genome. The activator proteins may act directly on recognition sites upstream of the viral promoter/enhancer sequence. Alternatively, the activator protein may interact with one or more other proteins which act on the recognition site to increase transcription. This activation of genes by an activator protein is often called transactivation.

It has also been found in a number of cases that an activating protein produced by one virus can act on recognition sites in other viruses or on certain cellular gene promoters to cause transactivation of the genes associated with the activation site.

References [1] to [30] listed in the attached bibliography are examples of the work done on transactivation, with particular reference to the Adenovirus E1A proteins.

The E1A region of adenoviruses encodes two major early proteins of 289 and 243 amino acids respectively. These are produced from two differently spliced mRNAs of 13S and 12S respectively. These E1A proteins are multifunctional and have been shown to play an essential role in cellular immortalization and transformation. The E1A gene product is also known to regulate the expression of certain viral and cellular genes in a positive or negative manner.

Figure 1:
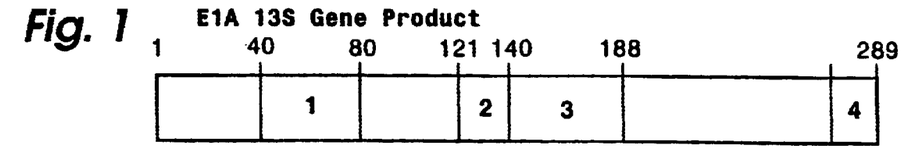
FIG. 1 shows diagrammatically the structure of the native E1A 289 protein.

The 289 and 243 proteins are identical except in that the 243 protein lacks a 46 amino acid region towards the centre of the 289 protein. The 289 protein has been investigated and several functions have been assigned to certain domains thereof. The 289 protein is shown in FIG. 1 to which reference is now made. Domain 1 mediates induction of DNA synthesis. Domain 2 mediates induction of mitosis, cellular immortalisation and transformation, and transcription repression. Domain 3 mediates indirect transactivation of viral and cellular genes. Domain 4 mediates nuclear localisation.

The mechanism for gene repression and cellular transformation is unclear, but point mutations within Domain 2 are able to abolish both repression and transformation without affecting the other functions.

WO-A-89/05862 (Invitron) describes the use of E1A to immortalise or extend the life of cells from primary cultures which would otherwise senesce after a limited number of cell generations in culture. In particular, the application describes the use of E1A to extend the lifespan of the human colon mucosa cells CCD 18 Co to allow continuous secretion of the tPA produced natively from these cells. This approach exploits the known immortalising—oncogene function of the 13S and 12S mRNAs from the E1A gene. It does not rely on transactivation.

More is known about the mechanism of transactivation, but even now the full mechanism has not been elucidated. It is known that the E1A 289 protein is phosphorylated and that somehow the active E1A protein induces phosphorylation of various DNA binding transcription factors, such as TFIId, ATF and TFIIIc, thus increasing their activity. It is conjectured that these activated transcription factors now bind to specific recognition sites, normally in homologous viral promoters, but also in mammalian genomic DNA sequences, to activate transcription from an associated promoter.

There have been various proposals for using transactivation to enable the production by recombinant DNA technology of a desired protein product. For instance, Grinnell et al. (see reference [19]) shows the production of a vector comprising the gene encoding human protein C (HPC) under the control of the adenovirus 2 late promoter in association with a BK virus (BKV) enhancer region. Another vector comprising the gene for the E1A 289 transactivator protein under the control of a BKV enhancer and promoter region is also used. The two vectors were used to cotransfect a human cell line. Cotransfection led to a 10 to 15 fold increase in HPC expression as compared to transfection with the first vector alone.

The system described by Grinnell [19] can be regarded as being essentially homologous, in that both BKV and adenoviruses are human viruses, the protein to be expressed is a human protein, and the host cell used for expression is a human cell. Despite the use of a homologous system, the level of expression achieved by Grinnell using the transactivator is relatively low.

U.S. Pat. No. 4,740,461 (Kaufman) generally relates to the use of amplifiable markers for increasing the yield of a desired protein. However, in Example 8, there is a description of the construction of a transcriptionally activated (transactivated) vector. The constructed vector contains an adenovirus 2 early region-2 (E2) promoter which is transcriptionally activated by the E1A gene transactivator protein. The adenovirus E2 promoter is used in separate vectors to control genes encoding DHFR and tPA. The E1A gene used is a fragment of total adenovirus. CHO cells are transfected with the two vectors and with the E1A gene. It is shown that the level of tPA production is decreased from 0.008 mU/cell/day to 0.0003 mU/cell/day if the E1A gene is omitted. However, even though an increased level of tPA production is achieved in the presence of E1A protein, the absolute level of tPA production is still relatively low. For instance, a CHO cell line transfected with a tPA gene under the control of the adenovirus major late promoter and SV40 enhancer can produce tPA at a level of 0.09 mU/cell/day without amplification or transactivation, and after selection for vector amplification can produce 6 mU/cell/day [35] or up to 10 mU/cell/day [U.S. Pat. No. 4,740,461].

WO88/07083 (Draper) generally relates to the use of transactivators for increasing the level of production of a desired protein. Although the disclosure is couched in general terms, and refers to such transactivators as ICP4, ICP0 and ICP27 from herpes simplex virus (HSV), PRV-IE gene product from pseudorabies virus, E1A from adenovirus and HCMV-MIE protein from human cytomegalovirus, the main thrust of the disclosure relates to the use of the Vmw65 transactivator protein from HSV. It is to be noted that when referring to transactivators apart from the Vmw65 protein, the Draper application indicates that "the structures, sequences or precise mechanism of action of the activation-reception sites for these stimulatory factors have not been fully elucidated".

It is also to be noted that, although the Draper application shows that the use of the vmw65 protein can lead to enhanced levels of production, there are no absolute values given for the production level. It is therefore not clear whether the use of the Vmw65 protein system can give rise to a commercially viable expression system.

There are a number of reports of the insertion of adenovirus E1A genes into mammalian cultured cells to generate permanent E1A-expressing cell lines. For instance, Babiss et al. (reference [1]) transfected human BK cells with DNA containing and E1 region of adenovirus and could identify clones expressing E1A only, E1B only or both. Babiss et al. used the cloned cell lines to investigate the action of the adenovirus by carrying out complementation experiments.

Roberts et al. (reference [7]) used retroviral vectors to introduce DNA sequences encoding the 13S, 12S or 9S E1A mRNAa into mouse NIH-3T3 cells. Transfected cells expressing the 13S product could complement a mutant adenovirus defective in E1A function, thus demonstrating transactivation of E1B, E2, E3 and E4 promoters in the adenovirus. Effects on endogenous cellular gene expression were also noted. Some proteins were slightly induced while others, such as collagen and fibronectin, were repressed.

Bergman and Shavit (reference [29]) also transfected the E1A gene into NIH-3T3 cells and derived permanent E1A expressing cell lines. These cells were able to activate an immunoglobulin light chain (κ) promoter/enhancer in transient expression assays using a CAT reporter gene.

None of Babiss et al., Roberts et al and Bergman and Shavit in any way contemplated using the cloned cell lines for the commercial production of desired proteins by recombinant DNA technology.

Thus, there is an indication that the E1A gene can be introduced into cultured mammalian cells where its expression is compatible with continued cell proliferation and where it continues to function as a transactivator of transiently transfected or infected DNA. However, there is nothing in any of these reports which in any way suggests that transactivation could be useful in increasing production from genes inserted permanently into eukaryotic cell lines. Indeed, there are suggestions that this would not be feasible.

For instance, Brady et al [43] demonstrated that a transiently transfected rat insulin gene is activated in 293 cells although the chromosomal gene is not activated. The authors suggest that cellular insulin genes are in a chromosomal environment inaccessible to E1A or its associated transcription machinery. Alwine (reference [5]) provides evidence that, although transient expression from plasmids introduced into the adenovirus-transformed human 293 cell line is substantially higher than in cell lines not containing adenovirus sequences (see reference [3]), the principal cause of increased transient expression is greatly enhanced stability of extrachromosomal plasmid DNA. The increased stability is not solely due to E1A or E1B expression. Such an effect of increasing stability would not be observed in a permanently transfected cell line in which the DNA was integrated into the host genome.

Weisshaar (see reference [26]) used E1A in transient transfection experiments to reactivate an E2A promoter which was integrated into the genome of an adenovirus-transformed BHK cell line and which had become inactivated by methylation on initial integration. Reactivation was only partial if E1A was used alone. E1B was required in addition to E1A in order to achieve increased levels of expression from the E2A promoter. In a subsequent paper by the same group (Knüst et al.—reference [30]) it was shown that in adenovirus-transformed BHK cells, there is a constitutive level of endogenous E1A expression which, although detectable, is insufficient to reactivate the chromosomally integrated E2A gene.

The evidence of these papers therefore indicates that whereas E1A can activate transfected genes effectually in transient expression experiments, chromosomally located genes are only poorly activated, if at all. The levels of expression reported would not be commercially significant.

There is therefore a need for an expression system using transactivators which produces commercially viable quantities of a desired protein from a permanent cell line.

Accordingly, the present invention provides a method of producing a desired protein which comprises permanently transfecting a eukaryotic host cell with:

a first transcription unit containing a gene encoding a transactivator protein or a mutant thereof under the control of a promoter/enhancer region; and a second transcription unit containing a gene encoding a desired protein under the control of a promoter/enhancer region which can be transactivated by the protein expressed by the first transcription unit, wherein the promoter/enhancer region in the first transcription unit is selected so that the amount of transactivator protein expressed from the first transcription unit is not enough to prevent cell growth but is sufficient to transactivate the promoter/enhancer region in the second transcription unit so that the desired protein is expressed at a level at least twice that which would be obtained from the same cell but lacking the first transcription unit.

Preferably, the amount of desired protein expressed is at least five, the preferably ten, times that which would be obtained from the same cell but lacking the first transcription unit.

The promoter/enhancer region in each transcription unit is preferably a viral region, although exogenous eukaryotic promoter/enhancer regions may also be used.

Preferably, the gene in the first transcription unit encodes the E1A protein or a mutant thereof. However, any other viral transactivator protein, such as the Vmw65, ICP4, ICP0, ICP27, PRV-IE and HCMV-MIE proteins referred to above, mutants thereof, viral or other oncogene or proto-oncogene products such a myc, fos or jun, or mammalian cellular activators such as protein kinase A, protein kinase C or NFκB, may be encoded by the first transcription unit.

In one alternative, the gene in the first transcription unit encodes the complete E1A 289 protein, in which case all four of its domains may be present. In another alternative, the first transcription unit encodes a mutant E1A 289 protein in which the amino acid sequence of the protein in one or more of domains 1, 2 and 4 has been altered in order to abolish or modify the activity of the or each domain. In a further alternative, the first transcription unit encodes a mutant E1A 289 protein which is substantially shorter than the native E1A protein.

Specific examples of mutant E1A 289 proteins which may be encoded by the gene in the first transcription unit are an E1A 289 protein in which mutations in Domain 2 have been made to abolish its repression function and an E1A 289-derived protein comprising the sequence of native Et1A protein from amino acid residues 139 to 289.

Preferably, the promoter in the first transcription unit is under the control of a weak promoter, such as the SV40E or SV40L promoter. Specific combinations which are preferred for the first transcription unit are the E1A gene under the control of the SV40E promoter and the R1176E1A gene (which is described below) under the control of the Sv40L promoter.

The promoter/enhancer region in the second transcription unit may be derived from any virus or cellular gene which includes a transactivator protein recognition site, the transactivator protein being one which is produced by or activated by the protein product of the gene in the first transcription unit. Such viruses include the adenoviruses (from one of which the E1A protein itself is derived) and the cytomegaloviruses (CMV), such as the human CMV (hCMV). In hCMV, the promoter/enhancer may be derived from the major immediate early gene. The selection of the promoter/enhancer region to be used in the second transcription unit will depend on the product of the gene in the first transcription unit and on the promoter/enhancer used in the first transcription unit.

Preferably, the promoter in the second transcription unit is a CMV-MIE promoter, especially when the gene in the first transcription unit encodes an E1A-derived protein.

The promoter/enhancer region in the first transcription unit may be any one of those referred to in the preceding paragraph, but will not necessarily be the same as or different from the promoter/enhancer region in the second transcription unit.

Particularly preferred combinations for use in the method of the present invention are, in the first transcription unit, either the E1A gene under the control of the SV40E promoter or the R1176E1A gene under the control of the SV40L promoter and, in the second transcription unit, the hCMV-MIE promoter controlling the gene for the desired protein.

The protein encoded by the gene in the second transcription unit may be, for instance, tissue plasminogen activator (tPA), tissue inhibitor of metalloproteinases (TIMP), human growth hormone (hGH), insulin, and interferon, chymosin, calcitonin gene related polypeptide (CGRP) or an immunoglobulin heavy or light chain polypeptide, including chimeric, humanized and hybrid Ig polypeptides. It should be noted that this list is by no means exclusive and it will be readily apparent to the skilled person that any desired protein can be produced by the process of the present invention. The gene may encode only the protein sequence or may encode a pro- or prepro- protein.

It has been found by the present inventors that optimisation of the expression level of the activator is essential for obtaining a commercially useful level of expression of the desired protein. For instance, it has been found that, if native or mutant E1A gene products are expressed from a strong promoter, the transfection efficiency is reduced and the level of production from the surviving clones is not increased, which is contrary to expectations. It was envisaged that the more E1A protein produced, the more efficient would be transactivation, at least until a plateau of expression is reached. The results of transient expression experiments support this hypothesis since the stronger the promoter used to express the activator, the greater the transactivation in transient expression. However, in stable cell lines, relatively inefficient expression of the transactivator gene is required for optimal transactivation. In light of the findings of the present inventors, it is conjectured that overproduction of the activator is inhibitory to cell growth. Appropriate expression levels of activator can readily be obtained by choice of a suitable promoter/enhancer for the first transcription unit.

It is clear that it is not possible to use the results from transient expression systems to predict the effects of using the same transcription unit in stable cell lines. Thus, a skilled person investigating transactivation using transient expression systems would not have been led to the concepts underlying the present invention.

A further result which was not predicted is that a strong promoter can be used with a truncated version of the E1A 289 protein comprising only amino acids 139–289 of the native protein to achieve significant activation.

It will be appreciated that the observations made by the inventors and set out in this specification enable the skilled man to select the appropriate combination of promoter/enhancer regions and transactivator protein or mutant gene to enable a satisfactory level of desired protein to be produced.

It has surprisingly been found that transactivation can occur even if a strong promoter, such as the hCMV major immediate early promoter/enhancer, is used for the second transcription unit. It is generally considered that such promoters are already operating at optimal efficiency and that they could not be activated further. The present inventors have shown that this is not the case and have thus shown, surprisingly, that production from a single copy of a gene controlled by a strong promoter can be increased significantly, thus allowing commercially useful amounts of product to be obtained from low copy number vectors.

The eukaryotic host cell used may be a yeast cell, such as an *S. Cerevisiae* cell, but is preferably an animal cell such as an insect or mammalian cell. Suitable cells include CHO cells, L cells, HeLa cells and human or rodent lymphoid cells such as myeloma cells or hybridoma cells. Preferably the host cells are CHO or lymphoid cells.

The two transcription units may be present on a single vector, in which case the host cell will be transfected with the one vector to produce a suitably transfected host cell.

However, it is preferred that the two transcription units are present on separate vectors. In this case, the host cell may be simultaneously cotransfected with both vectors. Preferably, however, the host cell is transfected sequentially with the vectors. This will enable the production of a transactivated host cell line suitable for transfection by any one of a number of vectors encoding different desired proteins. Thus, the host cell will firstly be transfected with a vector containing the transactivator protein gene under control of a selected promoter/enhancer region. Thereafter, the cell can be transfected with a vector containing the second transcription unit wherein the gene for the desired protein is under the control of a promoter/enhancer region, for instance that of the hCMV-MIE gene, selected in accordance with the structure of the first transcription unit.

The or each vector containing the first and second transcription units may be, for instance, based on plasmids or on phages. Methods for producing such plasmid or phage vectors are well known in the art and are described, for instance, by Maniatis et al. [32].

In the transfected or cotransfected host cells, the first and second transcription units are integrated into the chromosomal material of the host cells.

In order to produce the protein, the transfected or cotransfected host cell will be cultured under appropriate conditions to cause the host cell to express the desired protein. Preferably, the host cell is selected such that the desired protein is correctly processed, for instance by glycosylation or removal of pro or prepro sequences, and secreted. Suitable methods for culturing transfected host cell lines are described by Bebbington and Hentschel [31].

According to another aspect of the present invention, there is provided a eukaryotic host cell which has been permanently transfected with a first transcription unit containing a gene encoding a transactivator protein or a mutant thereof under the control of a promoter/enhancer region which is selected so that the amount of transactivator protein expressed from the first transcription unit is not enough to prevent cell growth but is sufficient to transactivate the promoter/enhancer region in a selected second transcription unit so that a desired protein is expressible from said second transcription unit at a level at least twice that which would be obtained from the same cell containing said second transcription unit but lacking the first transcription unit.

The promoter/enhancer region in the first transcription unit is preferably of viral origin.

Preferably, the host cell is an animal, most preferably a mammalian cell such as a CHO or NSO cell. Where the host cell is derived from a CHO cell, it is preferred that its transcription unit should produce E1A or an E1A-derived transactivator protein. Most preferably, it should produce between 10 and 40%, particularly between 15 and 25%, for example about 20%, of the amount of mRNA encoding the transactivator protein as is produced by the 293 cell line (ATCC CRL 1573) referred to in reference, and further deposited on behalf of Lonza Group Ltd., on Jun. 19, 2002, with the ATCC, 10801 University Blvd, Manasas, Va. 20110-7209 (Telephone No. 703-365-2700; Facsimile No. 703-365-2745) and assigned Patent Deposit Designation PTA-4488.

The present invention also provides transactivated host cells, vectors for use in producing such host cells, and host cells transfected with both transcription units.

The present invention is now described, by way of example only, with reference to the accompanying drawings, in which.

In the following Examples all secretion rates are given in units of micrograms of protein per million cells per day unless otherwise indicated.

Vector Construction

Figure 2:
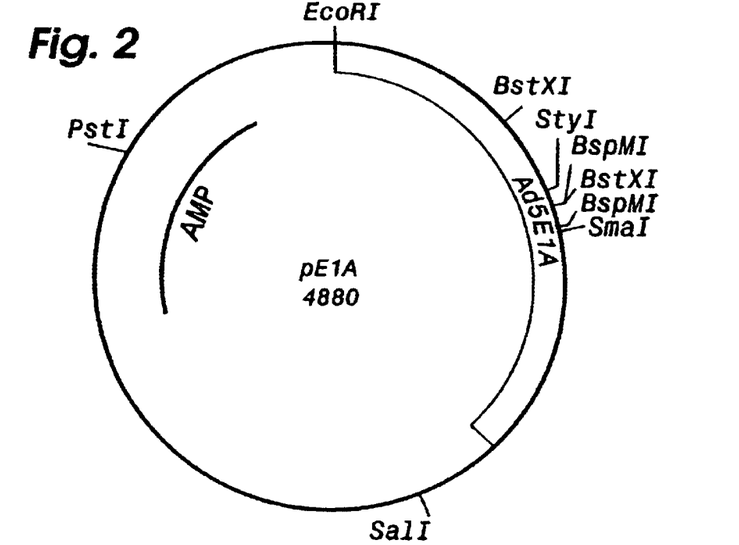
FIG. 2 shows diagrammatically the structure of the plasmid pE1A.

Plasmid pE1A, which is shown in FIG. 2, was used in the experiments described below. It comprises base pairs 1 to 1834 of adenovirus 5 DNA cloned into plasmid pML between its EcoRI and BamHI sites as described in reference [33]. The adenovirus segment includes the adenovirus E1A gene and promoter. In the following, this plasmid is referred to as E1A/E1A.

A gene encoding the E1A 289 protein which has been mutated to abolish its repressor function was produced by site directed mutagenesis in M13 using an oligonucleotide of the sequence.

5' ACC TGC CAC GGG GCT GGC TTT 3'.

This changes amino acid 126 in the E1A 289 protein from a glutamic acid to a glycine residue. This is referred to hereinafter as the R1176E1A gene in plasmid pR1176E1A.

A gene encoding amino acid residues 137 to 289 of the native E1A 289 protein was produced by isolating a 1140 bp BspmI to SalI fragment from plasmid pE1A and ligating this to a HindIII to SalI cut pSP64 vector [34] together with two synthetic oligonucleotides of the sequences 5' AGC TTC CAC CAT GGG AGA GGA GTT TGT GTT AGA TTA TGT GGA GCA CCC CGG 3' and

5' GTG CCC GGG GTG CTC CAC ATA ATC TAA CAC AAA CTG GTC TCC CAT GGT GGA 3' to form the gene referred to hereinafter as the t1A gene as pSP64t1A. The oligonucleotides add a concensus translation initiation sequence CCA CCA TG upstream of the codon for E1A residue 137.

In order to replace the natural E1A promoter upstream of the E1A and R1176E1A genes, the E1A promoter was removed from pE1A and pR1176E1A and a HindIII site inserted upstream of the E1A and R1176E1A genes. This was achieved by isolating a 4 kb EcoRI, partial BstXI fragment from the E1A and R1176E1A plasmids and ligating these with two oligonucleotides of the sequences 5' AAT TCA AGC TTC CAC CAT GAG ACA TAT TAT CTG GCA CGG AGG TGT TAT TAC CGA AGA AAT GGC CGC CAG TCT T 3' and 5' CTG GCC GCC ATT TCT TCG GTA ATA ACA CCT CCG TGC AGA TAA TAT GTC TCA TGG TGG AAG CTT G 3'.

This creates promoterless E1A and R1176E1A genes with a unique HindIII site and concensus translation initiation sequence upstream of the E1A and R1176E1A genes, creating plasmids pR1265/6 E1A and pR1265/6R1176E1A The following promoter/enhancer regions are available and HindIII cassettes:

hCMV—human cytomegalovirus major immediate early promoter [36, 37];

SV40E—simian virus 40 early promoter [39]; and

SV40L—simian virus 40 late promoter [39].

Both SV40 promoter consist of the 353 bp PvuII to HindIII fragment of SV40 (nucleotides 270 to 517) with a HindIII linker attached to the PvuII site. These promoters were inserted in the appropriate orientation upstream of the t1A in pSP64t1A and promoterless E1A and R1176E1A genes in plasmids pR1265/6E1A and pR1265/6R176E1A described above at their unique HindIII sites.

In this manner, the following promoter/enhancer-gene combinations were produced

| Promoter | Gene |
|----------|------|
| E1A | E1A |
| hCMV | E1A |
| SV40E | E1A |
| E1A | R1176E1A |
| hCMV | R1176E1A |
| SV40E | R1176E1A |
| SV40L | R1176E1A |
| hCMV | t1A |
| SV40E | t1A |
| SV40L | t1A |

Figure 3:
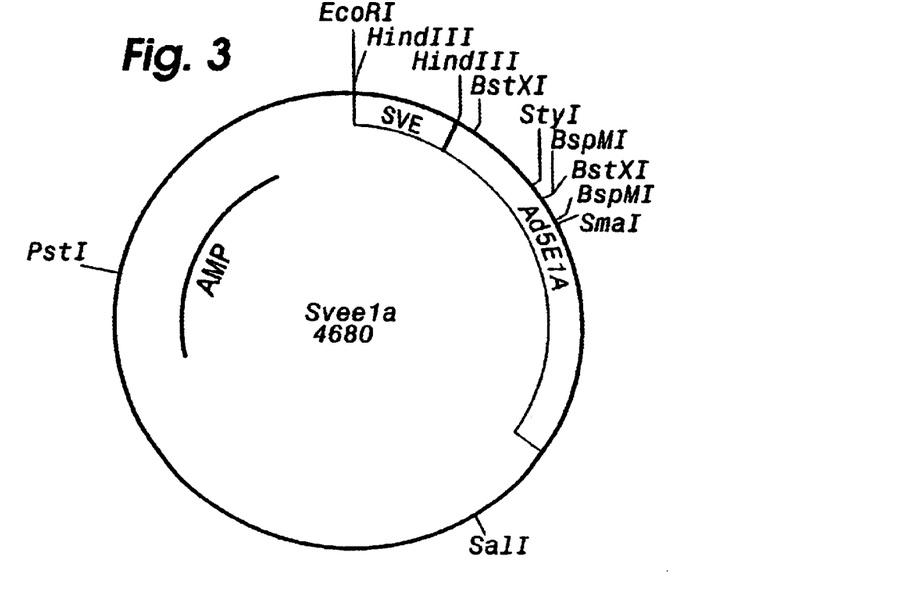
FIG. 3 shows diagrammatically the structure of the plasmid psVEE1A.
Figure 4:
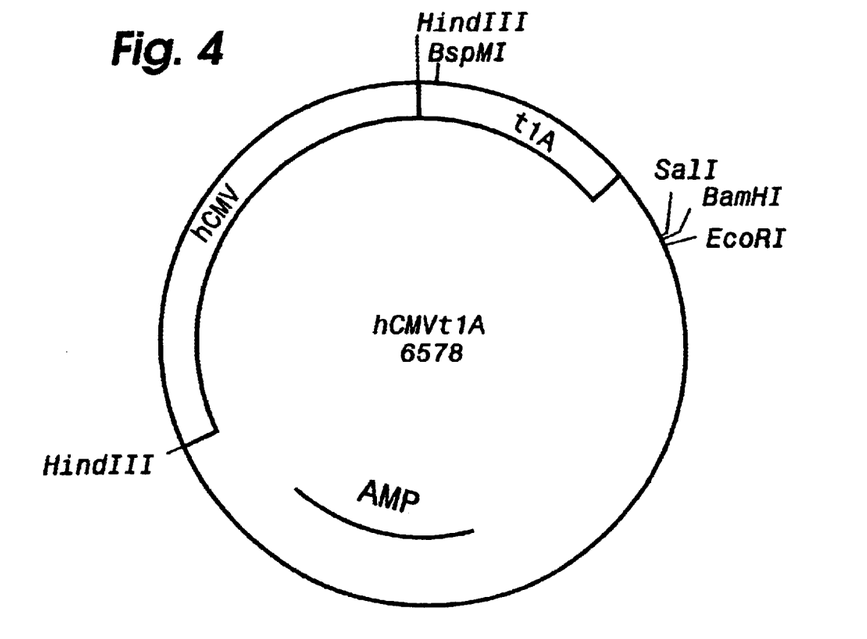
FIG. 4 shows diagrammatically the structure of the plasmid phCMVt1A.

The plasmid containing SV40E/E1A (pSVEE1A) is shown in FIG. 3. The plasmid containing hCMV/t1A (phCMVt1A) is shown in FIG. 4.

In order to construct the human procollagenase expression vector pHCollGS the procollagenase cDNA [40] was modified by standard techniques to produce a HindIII to BamHI fragment containing the complete procollagenase coding sequence. This fragment was inserted into pEE7 (pEE6 with the SV40 late promoter [39]) between the HindIII and BclI sites in the polylinker to produce pEE7collagenase. The hCMV promoter [39] was inserted as a HindIII fragment into the HindIII site adjacent the procollagenase cDNA so as to direct transcription of procollagenase to form pEE7hCMVcollagenase. The SV40 late-glutamine synthetase (GS) minigene from pSVLGS1 [31] was then inserted at the BamHI site 3' of the procollagenase cDNA as a 5.5 kb BamHI to PvuI fragment with the addition of a BamHI linker to the PvuI site. The GS minigene was arranged to transcribe in the same direction as procollagenase. This creates the vector pHCollGS.

The vector EE7Salne was constructed by taking the Bamne fragment from pSV3Bne [41], converting this to a SalI fragment by standard techniques and inserting this into the SalI site of EE7 [39].

The HIVlgp120 expression vector pEE6hCMVgp120GS was constructed as follows. The 3113 bp SalI to XhoI fragment of HIV1 3B BH10 [42] encoding the env gene was inserted into SalI cut pSP64 such that the pSP64 EcoRI site is positioned 3' to the env gene. This fragment was further modified by insertion of a stop codon at amino acid 511 by site directed mutagenesis and inserted of an EcoRI site immediately upstream of the env translation initiation codon. This resulted in an EcoRI fragment encoding the gp120 region of the HIV1 env gene. This EcoRI fragment was then inserted into the unique EcoRI site of pEE6hCMV [39] such that the gp120 gene would be transcribed by the hCMV promoter to give the vector pEE6hCMVgp120. The GS minigene described above was inserted as a 5.5 kb BamHI fragment into the BamHI site 3' of the gp120 gene so as to be transcribed in the same direction as gp120 to form the vector pEE6hCMVgp120GS.

EXAMPLE I

Figure 5:
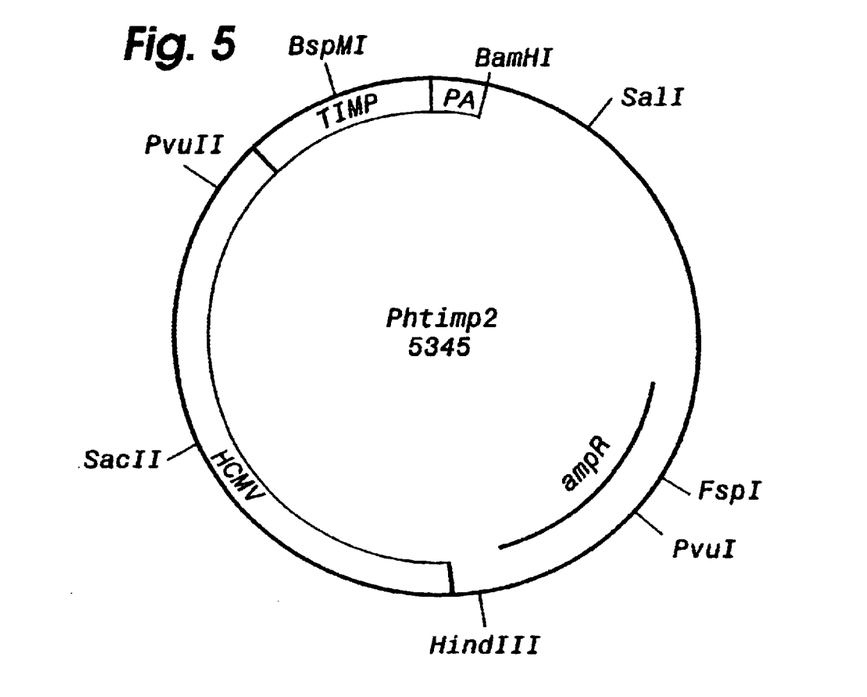
FIG. 5 shows diagrammatically the structure of the plasmid pHTIMP2.
Figure 6:
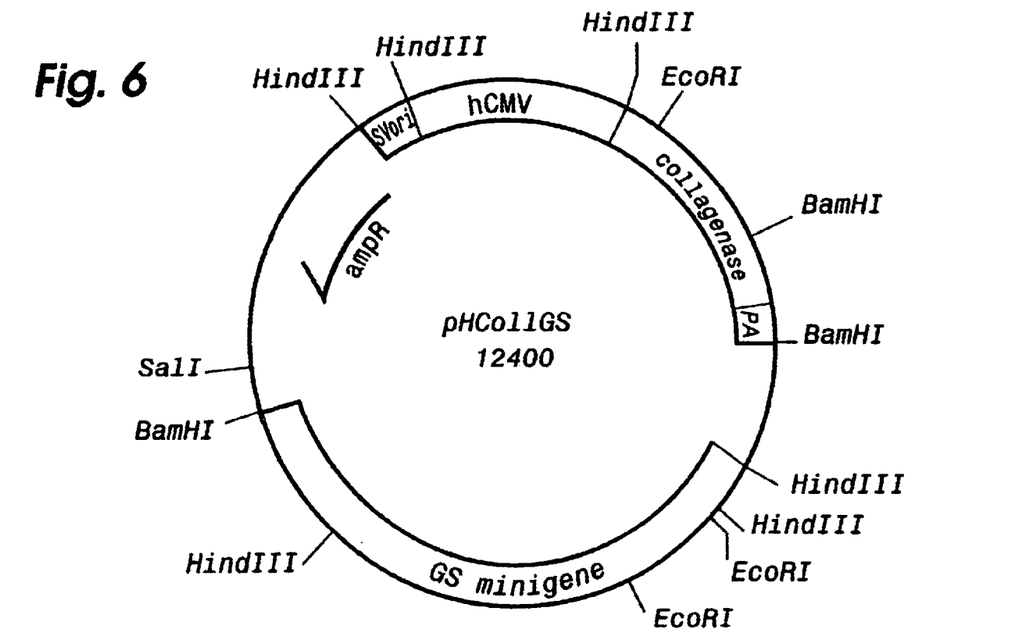
FIG. 6 shows diagrammatically the structure of the plasmid pHCollGS.
Figure 7:
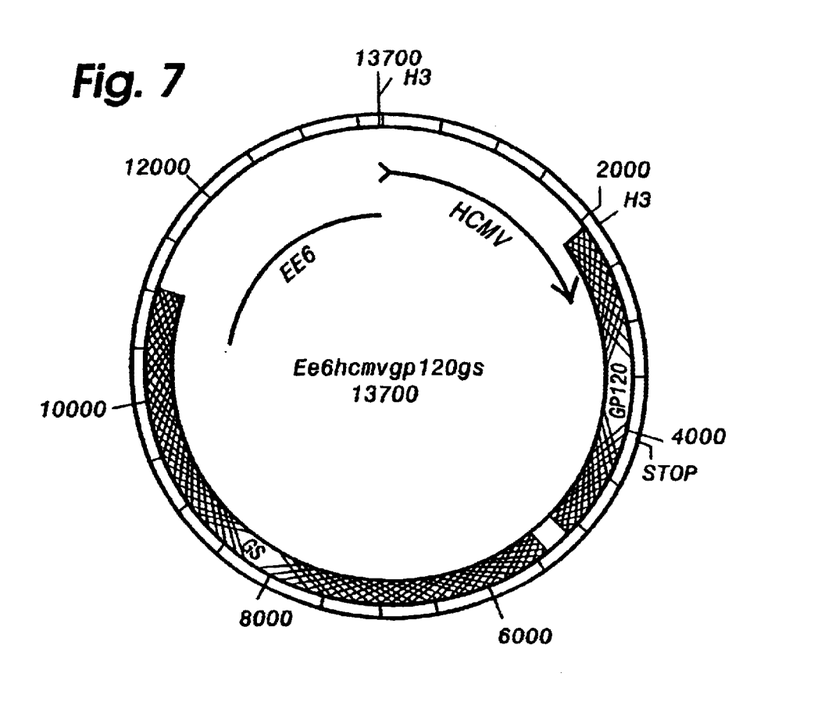
FIG. 7 shows diagrammatically the structure of the plasmid pEE6hCMVgp120GS.

The promoter/enhancer—gene containing vectors described above were transfected by a calcium phosphate coprecipitation procedure with glycerol shock into CHO-K1 cells for transient expression experiments. A vector, pHTIMP2 (FIG. 5), previously described as pHT.1 [36], containing a gene for TIMP under the control of the hCMV promoter/enhancer, was included for each transfection. Supernatants were assayed for TIMP production over a 24 to 72 hour period. This transient expression system should demonstrate a raised level of TIMP if transactivation of the hCMV promoter/enhancer occurs. The results of the use of the transient expression system are shown in Table 1.

TABLE 1

| Plasmid(s) (co)transfected | Time of Sampling (h) | TIMP level in Supernatant ng/ml |
|---|---|---|
| hCMV-TIMP | 40 | 1.0 |
| hCMV-TIMP + E1A/E1A | 40 | 4.35 |
| hCMV-TIMP + SV40L/t1A | 40 | 2.25 |
| hCMV-TIMP + SV40E/t1A | 40 | 2.90 |
| hCMV-TIMP + hCMV/t1A | 40 | 4.10 |
| hCMV-TIMP | 48 | 2.4 |
| hCMV-TIMP + hCMV/E1A | 48 | 5.2 |
| hCMV-TIMP + E1A/E1A | 48 | 5.8 |
| hCMV-TIMP + hCMV/t1A | 48 | 2.5 |
| hCMV-TIMP + E1A/R1176E1A | 48 | 5.0 |
| hCMV-TIMP | 72 | 0.94 |
| hCMV-TIMP + E1A/E1A | 72 | 2.85 |
| hcMV-TIMP + E1A/R1176E1A | 72 | 2.35 |

It can be seen that the use of the E1A 289 protein or mutants thereof can cause transactivation in transient expression systems. Furthermore, the t1A genes under control of the hCMV promoter transactivate more efficiently than when under the control of SV40 promoters. This is consistent with the fact that the hCMV promoter is stronger than SV40 promoters in the absence of activators.

EXAMPLE II

In order to investigate transactivation in a stable cell line, each plasmid containing an E1A, R1176E1A or t1A gene was altered by inserting therein a gene encoding xanthine-guanine phosphoribosyl transferase (gpt), a selectable marker, as a SalI fragment into the unique SalI site present in all the vectors. The resulting vectors were transfected into the cell line GS TIMP 19.12. This is a CH0-K1 cell line containing a single intact copy of the TIMP gene under the control of the hCMV promoter/enhancer region. Its secretion rate is 9 units (as defined above). After selection for introduction of the vectors containing the gpt gene, colonies from each transfection which were resistant to 10 μg/ml of mycophenolic acid (MPA) were pooled and grown up for assay to determine their specific productivity of TIMP. The results are shown in Table 2.

TABLE 2

| Plasmid transfected into GS TIMP 19.12 | TIMP Secretion rate | Ratio of Secretion rate relative to GSTIMP19.12 |
|---|---|---|
| none | 9 | 1.0 |
| hCMV/E1A | 8.7 | 1.0 |
| hCMV/R1176E1A | 9.1 | 1.01 |
| SV40E/R1176E1A | 11.3 | 1.25 |
| E1A/E1A | 13 | 1.44 |
| SV40L/R1176E1A | 18.8 | 2.09 |
| E1A/R1176E1A | 18.8 | 2.09 |
| hCMV/t1A | 25 | 2.78 |
| SV40E/E1A | 48 | 5.33 |

It can be seen from these results that expressing the native E1A 289 protein from a strong promoter does not yield detectable transactivation, whereas the best increase in secretion rate is obtained using the native E1A 289 protein under the control of a weak promoter. This is surprisingly contrary to expectations derived from the transient expression data, which would have led one to expect that the more E1A 289 protein that is produced, the more the hCMV promoter would be transactivated. Since this is not the case, it can be seen that the mechanism of transactivation in permanently transfected cell lines by the E1A 289 protein is not simple.

The next highest increase in productivity is obtained using the t1A gene (truncated E1A 289 protein) expressed from a strong promoter. Transactivation is also obtained using the mutant E1A (R1176E1A) protein expressed from the SV40 late promoter, but is not significantly obtained with the SV40 early or hCMV promoters. This, again, is consistent with the suggestion that overexpression does not lead to optimal activation.

It can thus be seen from these results that it is essential to express an appropriate level of the E1A 289-derived transactivator protein or the region 2 mutant R1176E1A if reasonable levels of transactivation are to be achieved. The results set out above allow the skilled person to select the appropriate transactivation system for any desired expression system.

EXAMPLE III

To investigate the levels of transactivation in individual transfected clones, the pools referred to in Table 2 were cloned and their secretion rates were measured. The results are shown in Table 3.

TABLE 3

| GS19.12 TIMP E1A clones | TIMP Secretion rate |
|---|---|
| SVE/E1A.4 | 88 * |
| SVE/E1A.5 | 36 * |
| SVE/E1A.8 | 21 * |
| SVE/E1A.10 | 41 * |
| SVE/E1A.11 | 66 * |
| E1A/R1176E1A.13 | 30 * |
| E1A/R1176E1A.17 | 31 * |
| E1A/R1176E1A.14 to 16 | 0 |
| E1A/R1176E1A.18 | 0 |
| SVL/R1176E1A.28 | 53♣ |
| SVL/R1176E1A.35 | 51♣ |
| SVL/R1176E1A.25 | 0 |
| SVL/R1176E1A.27 | 0 |
| SVL/R1176E1A.31 | 50 * |
| SVL/R1176E1A.32 | 71 * |
| hCMV/t1A.37 | 23 |
| hCMV/t1A.38 | 35 |
| hCMV/t1A.42 | 29 |
| hCMV/t1A.44 | 27 |
| hCMV/t1A.45 | 28 |
| hCMV/t1A.48 | 24 |

* = mean of two independent assays.
♣ = mean of four independent assays

The clones obtained from transfection with SVE/E1A and SVL/R1176E1A vectors generate cell lines with secretion rates comparable to that of a vector amplified, TIMP-producing CHO cell line. Selection for GS gene amplification in the GS19 TIMP-secreting cell line has previously been shown to generate cell lines secreting up to 110 units. It is clear therefore that transfection with particular E1A or mutant E1A genes can yield cell lines with very substantially increased levels of secretion of recombinant product from low copy number vectors.

EXAMPLE IV

When comparing the GS19.12 host cell line with the best transactivated clone (SVE/E1A.4) it can be seen that the level of productivity has been raised about ten fold (from 9 to 88 units). It would be expected that a ten fold increase in productivity would be associated with a ten fold increase in the amount of TIMP RNA produced. In order to test this hypothesis, the amount of TIMP RNA in the SVE/E1A.4 and GS19.12 cell lines was compared using a Northern blot analysis. The results of this investigation indicates that the SVE/E1A.4 cell line produces about 5.5 times as much TIMP RNA as does the 19.12 cell line when using β-actin mRNA as a standard.

This experiment clearly shows that there is transactivation of the hCMV promoter. However, it also shows that the increased TIMP productivity cannot be accounted for by the increase in mRNA level. It is conjectured that there is at least one additional mechanism involved in the action of these E1A proteins. This may include a direct effect of E1A protein on translation, secretion of protein stability. Alternatively, an indirect effect of E1A protein may occur either through transcriptional activation of cellular genes affecting one or more of these processes or by modification of the cellular gene products.

It was also noted that the SVE/E1A.4 cells looked bigger than GS19.12 cells. On analysis of dry weight of a number of cells it was found that the SVE/E1A.4 cells were about 2–3 times heavier than GS19.12 cells. The results of the analysis are shown in Table 4. The facts that the Northern blot data shows an increase in TIMP mRNA concentration of between 2 and 8 fold (5.5±3) relative to β-actin and that the SVE/E1A.4 cells are 2–3 times larger than GS19.12 fully accounts for the increased secretion rate of ten fold per cell.

TABLE 4

| Cell Line | Mean dry wt per cell (pg)* |
|---|---|
| CHO-K1 | 375 ± 35 |
| GS19.12 | 320 ± 99 |
| 19.12 SVE/E1A.4 | 780 ± 310 |
| CHO.E3 | 270 ± 14 |
| CHO.L761 | 340 ± 42 |

*mean of 2 experiments

EXAMPLE V

A CHO-K1 cell line expressing a plasminogen activator under control of the hCMV promoter (clone 2C2-3) was transfected with each of the vectors used to assess transactivation of TIMP in clone GS 19.12 (as described above). This gave the same general pattern of increases in productivity as was seen with the GS 19.12 cell line.

EXAMPLE VI

The mouse myeloma cell line NS0 was transfected with a gene encoding a chimeric immunoglobulin light chain derived from monoclonal antibody B72.3. The gene for the light chain was under the control of the hCMV promoter. A clone producing 4 units was obtained and was designated clone B424.

Each of the vectors used to assess transactivation in CHO-K1 cells (as described above) was transfected by electroporation into B424 cells. Pools of MPA resistant colonies were isolated and their secretion rates determined. In this experiment the pool of cells containing the SV4OL/R1176E1A construct gave a four fold increase in secretion rate. Other E1A and mutant E1A constructs also demonstrated transactivation.

Upon reassay of the pools of B424 transfectants, the increase in secretion rate was 1.4 fold (see Table 5), the SVE/E1A and SVL/R1176E1A pools giving the highest increase in secretion rate. These pools were cloned out and the clones were re-analysed.

TABLE 5

| Cell-Pool | Secretion rate | Ratio♣ |
|---|---|---|
| B424 EE6GPT | 2.4 | 1.0 |
| B424 hCMV/E1A | 2.2 | 0.92 |
| 3424 SVE/E1A | 3.3* | 1.4 |
| B424 hCMV/R1176E1A | 2.1 | 0.88 |
| B424 SVE/R1176E1A | 2.8 | 1.2 |
| B424 SVL/R1176E1A | 3.2* | 1.3 |

*Pools cloned out
♣ relative to B424 EE6GPT

The highest producing clone, clone 21, isolated was from the B424 SVL/R1176E1A pool. Clone 21 had a productivity of 8.7±2.3 compared to a productivity of 3.9±1.7 from B424 transfected with EE6GPT, an approximately 2 fold increase.

EXAMPLE VII

The transient expression data in Example 1 suggest that the more E1A produced, the more efficient the transactivation of the hCMV promoter. However, in Example 2 the stable cell lines demonstrating efficient transactivation were made using E1A or R1176E1A under the control of a weak promoter. This, together with the fact that a lower transfection efficiency was obtained with stronger promoters upstream of E1A, led to the belief that overexpression of E1A maybe toxic. In order to test this, two experiments were carried out, firstly to examine the effect of increasing levels of E1A expression on the number of surviving transfectant colonies, and secondly to investigate the effect of increasing concentration of an E1A plasmid in a co-transfection.

In the first experiment, the cell-line GS19.12 was transfected with R1176E1A under the control of a variety of different promoters as shown in Table 6. The number of colonies obtained after selection for integration of the gpt gene is shown in Table 6. It can be seen that with increase in promoter strength there is a decrease in colony formation.

TABLE 6

| Vector Transfected into GS19.12 (10 μg DNA per dish) | No. of Colonies/10⁶ Cells |
|---|---|
| Mock | 0 |
| EE6GPT | 97 |
| Promoterless/R1176E1A GPT | 143 |
| SVL/R1176E1A GPT | 127 |
| SVE/R1176E1A GPT | 31 |
| hCMV/R1176E1A GPT | 17 |

(Promoter strength in CHO.K1 cells hCMV>SVE>SVL>Promoterless)

Twelve clones of the GS19.12 hCMV/R1176E1A GPT pool were isolated and tested for transactivation. It was observed that none of these clones exhibited any transactivation.

In the second experiment, CHO-K1 cells were co-transfected with a constant amount of a neo resistant plasmid, pEE7Salne (3 μg/10⁶ cells) and increasing amounts of either a promoterless R1176E1A vector or the hCMV/R1176E1A expression vector. The results are shown in Table 7 as number of colonies obtained after selection with selective agent G418 for 3 weeks. All transfections were done in duplicate and total colonies are shown.

TABLE 7

| E1A Vector Quantity μg/10⁶ Cells | Vector Co-transfected with Neo Plasmid | Colonies/ 2 × 10⁶ Cells |
|---|---|---|
| 0 | Mock | 0 |
| 0 | Positive Control (neo alone) | 49 |
| 0.5 | Promoterless R1176E1A | 42 |
| 2.0 | Promoterless R1176E1A | 24 |
| 10.0 | Promoterless R1176E1A | 34 |
| 0.5 | hCMV R1176E1A | 48 |
| 2.0 | hCMV R1176E1A | 14 |
| 10.0 | hCMV R1176E1A | 7 |

It can be seen from these results that increasing the concentration of a co-transfected E1A expressing vector reduces the transfection efficiency of the neo resistance vector when compared to co-transfection with a promoterless (non-expressing) E1A vector. This suggests that over expression of E1A is toxic.

EXAMPLE VIII

In order to isolate a new host CHO cell line constitutively expressing optimal levels of a transactivator, the two E1A expression vectors shown in Example 3 to be most efficient in transactivating the TIMP expression from GS19.12 (SVE/E1AGPT and SVL/R1176E1AGPT) were transfected into CHO-K1 cells by calcium phosphate co-precipitation and MPA resistant colonies were isolated 3–4 weeks later. 12 transfectants from each transfection were expanded and were tested for the ability to transactivate the hCMV promoter in a transient expression assay in order to carry out a rapid screening of the cell lines. Each cell line was plated out in duplicate into a 9 cm petri dish (2×10⁶ cells per dish). The vector pHTIMP2 was then transfected into each dish (3 μg per dish). Samples were taken 48 and 72 hours post-transfection and were assayed using TIMP ELISA. The results are shown in Table 8. The cell-lines CHOE6 and CHOL76-1 gave the highest level of TIMP expression in this transient assay.

TABLE 8

| Cell-Line | TIMP levels (ng ml₁) 48 hr | 72 hr |
|---|---|---|
| CHO E* | | |
| 1 | 2.9 | 3.9 |
| 2 | 7.2 | 9.6 |
| 3 | 6.4 | 7.2 |
| 4 | 2.5 | 4.8 |
| 5 | 5.0 | 5.8 |
| 6 | 60.0 | 80.0 |
| 7 | 8.66 | 9.0 |
| 8 | 7.6 | 10.0 |
| 9 | 3.5 | 5.0 |
| 10 | 0 | 0 |
| 11 | 11.0 | 13.5 |
| 12 | 13.5 | 17.0 |
| CHO L76⁺ | | |
| 1 | >100 | >>100 |
| 2 | 6.0 | 7.6 |
| 3 | 6.8 | 10.0 |
| 4 | 5.8 | 8.7 |
| 5 | 11.0 | 19.0 |
| 6 | 12.5 | 19.0 |
| 7 | 9.0 | 17.5 |

TABLE 8-continued

| Cell-Line | TIMP levels (ng ml₁) 48 hr | 72 hr |
|---|---|---|
| 8 | 17.0 | 22.0 |
| 10 | 9.6 | 13.0 |
| 11 | 12.0 | 16.0 |
| 12 | 8.6 | 10.0 |

*CHO E cell-lines are CHO-K1 cells transfected with SVE/E1A GPT
⁺CHO L76 cell-lines are CHO-K1 cells transfected with SVL/R1176E1A GPT These two cell lines together with CHO-K1 cells were reassayed by the same method and the results demonstrate that CHOE6 gave a 3 to 4 fold increase in TIMP expression and CH0L76-1 gave a 10 to 20 fold increase in TIMP expression relative to CHO-K1 cells.

The cell line CHOL76-1 was then cloned out and sub-clones were assayed by the same method, in comparison to CHO-K1 cells. All 12 clones analysed gave much higher levels of TIMP expression than CHO-K1 cells. CHOL76-1h, one of the clones, secreted 20 fold more TIMP than CHO-K1. This cell line has been used for many different transient expression experiments and consistently secretes high levels of protein, comparable to levels seen in COS-1 cells which are widely used for high level transient expression (Table 9). The cell line CHOL761h is also stable for at least 30 generations in the absence of selection as determined by transient expression.

TABLE 9

| Gene | Transient Expression Levels CHOL761h | COS-1 |
|---|---|---|
| mouse-human chimeric antibody | 1.13 ± 0.32 μg ml⁻¹ | 0.3 ± 0.17 μg ml⁻¹ |
| human TIMP | 2–3 μg ml⁻¹ | |
| human prostromelysin | 1.5 – 2.0 μg ml⁻¹ | |
| human procollagenase | 0.8 μg ml⁻¹ | |
| Y22 chimeric light chain | 1–2 μg ml⁻¹ | |
| PUK | 0.5 μg ml⁻¹ | |
| tPA | 0.5 μg ml⁻¹ | |

The cloned cell line CHOL76-1h was then used to generate permanent cell lines expressing recombinant products. The expression vectors pHCollGS (a human procollagenase expression vector) and pEE6hCMVgp120GS (which is capable of expressing the gp120 coat protein of HIV1) were introduced into both CHO-K1 and CHOL76-1 cells by calcium phosphate coprecipitation. These were selected in 25 μM MSX and transfectants were expanded for analysis 4 weeks after transfection. Table 10 shows secretion rates obtained from: the best 2 clones out of 24 analysed from CHO-K1 transfected with pHCollGS; the best 6 clones out of 33 analysed from CHOL761H transfected with pHCollGS; the best clone out of 60 analysed from CHO-K1 transfected with pEE6hCMVgp120GS; and the best clone out of 24 analysed from CHOL76-1 transfected with pEE6hCMVgp120GS. The initial CHOL761h transfectants in both cases express product at levels much higher than initial transfectants in CHO-K1 cells.

TABLE 10

| Cell-line/Clone | Secretion Rate |
| --- | --- |
| CHO-K1 + pHCollGS.9 | 0.03 |
| CHO-K1 + pHCollGS.11 | 0.16 |
| CHOL76-1h + pHCollGS.1 | 6.6 |
| CHOL76-1h + pHCollGS.2 | 11.4 |
| CHOL76-1h + pHCollGS.5 | 6.6 |
| CHOL76-1h + pHCollGS.7 | 5.8 |
| CHOL76-1h + pHCollGS.9 | 8.0 |
| CHOL76-1h + pHCollGS.10 | 13.1 |
| CHO-K1 + pEE6hCMVgp120GS.17 | 1.8 |
| CHOL76-1h + PEE6hCMVgp120GS ICE.5 | 4.8 |

It will be appreciated that the procedure set out in this Example can be employed, with appropriate variations, to any other selected cell system. The essence of the process, which is an important aspect of the present invention, is that the selected host cell is transfected with a variety of vectors, each containing a transactivator gene under the control of a promoter. Generally the promoter will be a weak promoter. The transfectants will then be screened using transient assays for transfectant cell lines which have the ability to activate the promoter of a second transcription unit to significant levels. The vectors which are selected using this procedure will then be used to establish permanent cell lines from which will be selected those cell lines which give increased expression of desired proteins from suitable vectors stably introduced into the cell line.

EXAMPLE IX

In order to define the levels of E1A required for efficient transactivation, RNA blots were analysed. Poly A$^+$ mRNA was prepared from 293 cells (a human cell line transformed with defective adenovirus that produces constitutive E1A mRNA), CHOL76-1h (the CHO cell line described in example 8), GS19.12 (the cell line described in Example 2 into which various E1A expression vectors were introduced), and GS19.12 SVL/R1176E1A.28, .31, .32 and .35 (the clones described in Example 3).

5 µg of each CHO cell line RNA was loaded onto a denaturing agarose gel together with 5, 2 and 0.5 µg of 293 cell RNA. The gel was blotted onto nitrocellulose and the blot was probed sequentially with:
  i. a 300 bp BstXI fragment of the Adenovirus type 5 E1A gene;
  ii. A 700 bp BamH1 to Pst1 mouse α-actin cDNA fragment [38]; and
  iii. a 1000 bp PstI fragment of a mouse cDNA encoding glyceraldehyde phosphate dehydrogenase (GAPDH).

The results for the 293 cell mRNA show a broad band of the correct size for 12 and 13S E1A mRNA that encode the two major E1A gene products. A decreasing signal is seen for these mRNA species with a decreasing amount of Poly A$^+$ mRNA loaded onto the gel.

The CHOL76-1h cell mRNA shows a band of the same molecular weight as that in 293 cells when probed with probe (i) and a faint band of higher molecular weight. The signal is about 20% (+20%, −10%) of that in the equivalent loading of E1A 293 cells. The negative control cell line GS19.12 has no detectable E1A mRNA, as expected. The 4 GS 19.12 SVL/R1176E1A cell line mRNA's have various amounts of E1A mRNA. Clones .28 and .31 have no apparent signal. Clone .32 has a signal about one fifth of that in the 293 cells and also has a few higher molecular weight bands. Clone .35 has a slightly lower level of E1A mRNA than GS 19.12 SVL/R1176E1A.32 and in addition the bands all migrate at an increased molecular weight which is not predicted. The actin and GAPDH probes used as control for RNA loading gave similar signals across all tracks.

The cell lines CHOL76-1h and 19.12 SVL/R1176E1A.32 are cell lines that give highest levels of transactivation as selected by two different routes. It appears that the levels of E1A or R1176E1A required in CHO-K1 cells for efficeint transactivation are between 15 and 25% of that seen in 293 cells.

For other cell types, the level of transactivator required may be different from that required in CHO cells. For instance, Example VI relates to the use of transactivators in NSO cells. To determine what level is optimum, the screening procedure referred to above may be carried out in order to determine that optimum level for each cell type.

It can thus be seen that the present invention enables the production at commercially useful levels of a desired protein from a single copy of the gene encoding the protein stably inserted into a eukaryotic host cell. Thus, it will be possible to avoid the use of amplification systems to enable the commercial production of desired proteins.

The present invention has been described above by way of illustration only, and it will be apparent to the skilled person that variations or modifications of detail may be made without departing from the scope of the invention.

REFERENCES

1. Babiss et al., J. Virol., 46, 2, 454–465, 1983.
2. Gaynor et al., PNAS-USA, 81, 1193–1197, 1984.
3. Svensson and Akusjärvi, EMBO J., 3, 4, 789–794, 1984.
4. Velcich and Ziff, Cell, 40, 705–716, 1985.
5. Alwine, Mol. Cell. Biol., 5, 5, 1034–1042, 1985.
6. Spaete and Mocarski, J. Virol., XX, 135–143, 1985.
7. Roberts et al., J. Virol, 56, 2, 404–413, 1985.
8. Berk, Ann. Rev. Genet., 20, 45–79, 1986.
9. Kovesdi et al., Science, 231, 719–722, 1986.
10. Lillie et al., Cell, 46, 1043–1051, 1986.
11. Grinnell et al., Mol. and Cell. Biol., 6, 11, 3596–3605, 1986
12. Moran and Matthews, Cell, 48, 177–178, 1987.
13. Lee and Green, EMBO J., 6, 5, 1345–1353, 1987.
14. Stein and Ziff, Mol. and Cell. Biol., 7, 3, 1164–1170, 1987.
15. Wu et al., Nature, 326, 512–515, 1987.
16. Rayachaudhuri et al., EMBO J., 6, 13, 4073–4081, 1987.
17. Kuppuswamy and Chinnadurai, Virology, 159, 31–38, 1987.
18. Lillie et al., Cell, 50, 1091–1100, 1987.
19. Grinnell et al., Bio/Technology, 5, 1189–1192, 1987.
20. Lee et al., PNAS USA, 84, 8355–8259, 1987.
21. Reichel et al., PNAS-USA, 85, 387–390, 1988.
22. Simon et al., Cell, 52, 723–729, 1988.
23. Webster et al., Nature, 332, 553–557, 1988.
24. Slavicek et al., The EMBO Journal, 7, 10, 3171–3180, 1988.
25. Tremblay et al., J. Biol Chem., 263, 13, 6375–6383, 1988.
26. Weisshaar et al., J. Mol. Biol., 202, 255–270, 1988.
27. Green et al., Cell, 53, 921–926, 1988.
28. Ptashne, Nature, 335, 683–689, 1988.
29. Bergman and Shavit, J. Immunol., 140, 6, 2073–2080, 1988.
30. Knüst et al., J. Virol., 63, 8, 3519–3524, 1989.
31. Bebbington and Hentschel, DNA Cloning, Vol III, 163–188, 1987.
32. Maniatis et al., Molecular Cloning, Cold Spring Harbor, N.Y., 1982.

33. Franza et al., Cell, 44, 409–418, 1986.
34. Melton et al., Nuc. Acids Res., 12, 7035–7056, 1984.
35. Kaufman et al., Mol. Cell. Biol., 5, 1750–1759, 1985.
36. International Patent Application No. PCT/GB88/00602.
37. Whittle et al., Protein Engineering, 1, 499–505, 1987.
38. Minty et al., J. Biol. Chem., 256, 1008–1014, 1981.
39. Stephens & Crockett 1989, Nuc. Acids Res., 17, 7110, 1989
40. Whitham et al., Biochem. J., 240, 913–916, 1986.
41. Kenten & Boss, International Patent Application No. WO 86/05807.
42. Ratner et al., Nature, 313, 277–284, 1986.
43. Brady et al., Cancer Cells, 1, 105–110, 1984.

What is claimed is:

1. A method of producing a desired protein which comprises
   i) stably transforming a eukaryotic host cell, selected from a CHO cell and a lymphoid cell, by transfection with:
      a first transcription unit containing a gene encoding a transactivator protein under the control of a promoter/enhancer region, wherein the gene in the first transcription unit encodes complete E1A289 protein, or the transactivator protein is a mutant E1A289 protein in which the amino acid sequence of the E1A289 protein in domain 2 thereof is altered, or a mutant E1A289 protein which is shorter than the complete E1A289 protein by up to 136 residues at the N-terminal end; and
      a second transcription unit containing a gene encoding said desired protein under the control of a promoter/enhancer region transactivatable by the transactivator protein expressed by the first transcription unit, wherein said promoter of the promoter/enhancer region of the second transcription unit is the HCMV-MIE promoter,
      wherein the promoter/enhancer region of the first transcription unit is selected so that the amount of transactivator protein expressed from the first transcription unit is not enough to prevent growth of said host cell but is sufficient to transactivate the promoter/enhancer region of the second transcription unit so that the desired protein is expressed at a level at least twice that which would be obtained from the same host cell but lacking the first transcription unit; and
   ii) culturing said host cell resulting from step i) under conditions such that said desired protein is produced.

2. The method of claim 1, wherein the amount of said desired protein expressed is at least five times that which would be obtained from the same host cell but lacking the first transcription unit.

3. The method of claim 1, wherein the amount of said desired protein expressed is at least ten times that which would be obtained from the same host cell but lacking the first transcription unit.

4. The method of claim 1, wherein the first and second transcription units are on separate vectors.

5. The method of claim 1, further comprising the step of harvesting the desired protein.

6. A method of producing a desired protein which comprises
   i) stably transforming a eukaryotic host cell, selected from a CHO cell and a lymphoid cell, by transfection with:
      a first transcription unit containing a gene encoding a transactivator protein under the control of a promoter/enhancer region, wherein the gene in the first transcription unit encodes complete E1A289 protein, or the transactivator protein is a mutant E1A289 protein in which the amino acid sequence of the E1A289 protein in domain 2 thereof is altered; and
      a second transcription unit containing a gene encoding said desired protein under the control of a promoter/enhancer region transactivatable by the transactivator protein expressed by the first transcription unit, wherein said promoter of the promoter/enhancer region of the second transcription unit is the HCMV-MIE promoter,
      wherein the promoter/enhancer region of the first transcription unit is selected so that the amount of transactivator protein expressed from the first transcription unit is not enough to prevent growth of said host cell but is sufficient to transactivate the promoter/enhancer region of the second transcription unit so that the desired protein is expressed at a level at least twice that which would be obtained from the same host cell but lacking the first transcription unit; and
   ii) culturing said host cell resulting from step i) under conditions such that said desired protein is produced.

7. A method of producing a desired protein which comprises
   i) stably transforming a eukaryotic host cell, selected from a CHO cell and a lymphoid cell, by transfection with:
      a first transcription unit containing a gene encoding a transactivator protein under the control of a promoter/enhancer region, wherein the transactivator protein is a mutant E1A289 protein in which the amino acid sequence of the E1A289 protein in domain 2 thereof is altered; and
      a second transcription unit containing a gene encoding said desired protein under the control of a promoter/enhancer region transactivatable by the transactivator protein expressed by the first transcription unit, wherein said promoter of the promoter/enhancer region of the second transcription unit is the HCMV-MIE promoter,
      wherein the promoter/enhancer region of the first transcription unit is selected so that the amount of transactivator protein expressed from the first transcription unit is not enough to prevent growth of said host cell but is sufficient to transactivate the promoter/enhancer region of the second transcription unit so that the desired protein is expressed at a level at least twice that which would be obtained from the same host cell but lacking the first transcription unit; and
   ii) culturing said host cell resulting from step i) under conditions such that said desired protein is produced.

8. A eukaryotic host cell, selected from a CHO cell and a lymphoid cell, stably transformed by transfection with a first transcription unit containing a gene encoding a transactivator protein under the control of a promoter/enhancer region, wherein the gene in the first transcription unit encodes complete E1A289 protein, or the transactivator protein is a mutant E1A289 protein in which the amino acid sequence of the E1A289 protein in domain 2 thereof is altered, or a mutant E1A289 protein which is shorter than the complete E1A289 protein by up to 136 residues at the N-terminal end; and
   a second transcription unit containing a gene encoding a desired protein under the control of a promoter/enhancer region transactivatable by the transactivator protein expressed by the first transcription unit, wherein said promoter of the promoter/enhancer region of the second transcription unit is the HCMV-MIE promoter, wherein the promoter/enhancer region of the first transcription unit is selected so that the amount of transactivator protein expressed from the first transcription unit is not enough to prevent growth of said host cell but is sufficient to transactivate the promoter/enhancer region of the second transcription unit so that the desired protein is expressed at a level at least twice that which would be obtained from the same host cell but lacking the first transcription unit.

9. The host cell of claim 8, wherein the first transcription unit produces between 10 and 40% of the amount of mRNA encoding the transactivator protein as is produced by cell line 293 deposited at the ATCC under deposit number PTA-4488 on Jun. 19, 2002.

10. An expression vector comprising a first transcription unit containing:

a gene encoding a transactivator protein under the control of a promoter/enhancer region wherein the transactivator protein is the E1A289 protein, a mutant E1A289 protein in which the amino acid sequence of the E1A289 protein in domain 2 thereof is altered, or a mutant E1A289 protein which is shorter than the complete E1A289 protein by up to 136 residues at the N-terminal end; and a second transcription unit containing a gene encoding a desired protein under the control of a promoter/enhancer region transactivatable by the transactivator protein expressed by the first transcription unit, wherein the promoter of the promoter/enhancer region of the second transcription unit is the HCMV-MIE promoter.

11. An expression vector comprising a first transcription unit containing:

a gene encoding a transactivator protein under the control of a promoter/enhancer region wherein the transactivator protein is the E1A289 protein or a mutant E1A289 protein in which the amino acid sequence of the E1A289 protein in domain 2 thereof is altered; and a second transcription unit containing a gene encoding a desired protein under the control of a promoter/enhancer region transactivatable by the transactivator protein expressed by the first transcription unit, wherein the promoter of the promoter/enhancer region of the second transcription unit is the HCMV-MIE promoter.

12. An expression vector comprising a first transcription unit containing:

a gene encoding a transactivator protein under the control of a promoter/enhancer region wherein the transactivator protein is the E1A289 protein and the promoter of said promoter/enhancer region is the SV4OE promoter, or the transactivator protein is a mutant E1A289 protein in which the amino acid sequence of the E1A289 protein in domain 2 thereof is altered and the promoter of said promoter/enhancer region is the SV40L promoter; and a second transcription unit containing a gene encoding a desired protein under the control of a promoter/enhancer region transactivatable by the transactivator protein expressed by the first transcription unit, wherein the promoter of the promoter/enhancer region of the second transcription unit is the HCMV-MIE promoter.

13. An expression system comprising two separate vectors, wherein the first vector comprises a first transcription unit containing a gene encoding a transactivator protein under the control of a promoter/enhancer region wherein the transactivator protein is the E1A289 protein or a mutant E1A289 protein in which the amino acid sequence of the E1A289 protein in domain 2 thereof is altered; and the second vector comprises a second transcription unit containing a gene encoding a desired protein under the control of a promoter/enhancer region transactivatable by the transactivator protein expressed by the first transcription unit, wherein the promoter of the promoter/enhancer region of the second transcription unit is the HCMV-MIE promoter.

* * * * *

UNITED STATES PATENT AND TRADEMARK OFFICE
CERTIFICATE OF CORRECTION

PATENT NO. : 6,653,101 B1
DATED : November 25, 2003
INVENTOR(S) : Cockett et al.

It is certified that error appears in the above-identified patent and that said Letters Patent is hereby corrected as shown below:

<u>Title page,</u>
Item [73], Assignee, should read -- Lonza Group AG, Zurich (CH) --

Signed and Sealed this

Twenty-seventh Day of April, 2004

JON W. DUDAS
*Acting Director of the United States Patent and Trademark Office*